United States Patent
Weydahl

(10) Patent No.: US 9,217,184 B2
(45) Date of Patent: Dec. 22, 2015

(54) PROCESS FOR THE PRODUCTION OF ALCOHOLS

(75) Inventor: Karl Ragnar Weydahl, Bergen (NO)

(73) Assignee: WEYLAND AS, Blomsterdalin (NO)

(*) Notice: Subject to any disclaimer, the term of this patent is extended or adjusted under 35 U.S.C. 154(b) by 887 days.

(21) Appl. No.: 13/318,302

(22) PCT Filed: Apr. 20, 2010

(86) PCT No.: PCT/GB2010/000791
§ 371 (c)(1),
(2), (4) Date: Jan. 10, 2012

(87) PCT Pub. No.: WO2010/128272
PCT Pub. Date: Nov. 11, 2010

(65) Prior Publication Data
US 2012/0190840 A1    Jul. 26, 2012

(30) Foreign Application Priority Data

May 7, 2009    (GB) .................................. 0907879.1

(51) Int. Cl.
*B01D 11/04* (2006.01)
*C12P 7/10* (2006.01)
(Continued)

(52) U.S. Cl.
CPC .............. *C13K 1/02* (2013.01); *B01D 11/0426* (2013.01); *B01D 11/0488* (2013.01);
(Continued)

(58) Field of Classification Search
CPC .... B01D 11/00; B01D 11/04; B01D 11/0426; B01D 11/0492; B01D 11/043; B01D 2011/002; B01D 11/0488; C07C 29/09; C07C 29/86; C07C 29/128; C07H 1/06; C07H 3/06; C12P 7/06; C12P 7/08; C12P 7/10; Y02E 50/16; Y02E 50/17; Y02E 50/18; C13K 1/02

USPC ............ 44/307, 313, 589, 605; 210/202, 209, 210/259, 511, 634, 639, 749, 773, 806; 422/187, 256; 536/127, 128; 568/902; 530/422, 427

See application file for complete search history.

(56) References Cited

U.S. PATENT DOCUMENTS 2,121,318 A * 6/1938 Evans ........................ 196/14.52
2,356,500 A * 8/1944 Boinot ............................ 127/37
(Continued)

FOREIGN PATENT DOCUMENTS

CN        101157445       4/2008
EP        0018621 A       11/1980
(Continued)

OTHER PUBLICATIONS

US Patent & Trademark Office, Office Action and Notice of References Cited issued Nov. 15, 2013 in co-pending U.S. Appl. No. 13/122,296.
(Continued)

*Primary Examiner* — Joseph Drodge
(74) *Attorney, Agent, or Firm* — Iphorgan Ltd.

(57) ABSTRACT

The invention provides a process for alcohol production from a cellulosic material wherein a said cellulosic material is subjected to acid hydrolysis to yield an aqueous hydrolysate, said hydrolysate is introduced into a separator at a hydrolysate inlet, an extraction solvent is introduced into said separator at at least two extraction solvent inlets, a residue containing oligosaccharides is removed from said separator at a residue discharge outlet, and acid-containing extraction solvent is removed from said separator at an extraction solvent discharge outlet, wherein removal of said extraction solvent from said separator through said discharge outlet occurs downstream of at least one said extraction solvent inlet and upstream of at least one other said extraction solvent inlet.

27 Claims, 5 Drawing Sheets

(51) Int. Cl.
    *C13K 1/02*             (2006.01)
    *C07C 29/09*          (2006.01)
    *C07H 1/06*            (2006.01)
    *B01D 11/00*          (2006.01)

(52) U.S. Cl.
    CPC .............. *B01D 11/0492* (2013.01); *C12P 7/10* (2013.01); *B01D 2011/002* (2013.01); *C07C 29/09* (2013.01); *C07H 1/06* (2013.01); *Y02E 50/16* (2013.01)

(56) References Cited

U.S. PATENT DOCUMENTS

| | | | |
|---|---|---|---|
| 2,477,087 A | | 7/1949 | Robertson |
| 2,851,395 A | * | 9/1958 | Kiersted, Jr. et al. ......... 208/318 |
| 3,212,933 A | * | 10/1965 | Hess et al. ....................... 127/37 |
| 3,228,985 A | | 1/1966 | Carpenter |
| 4,028,462 A | * | 6/1977 | Domic et al. ................... 423/24 |
| 4,237,110 A | | 12/1980 | Forster et al. |
| 4,325,888 A | * | 4/1982 | Hildon ............................. 562/2 |
| 4,375,387 A | | 3/1983 | DeFilippi |
| 4,608,245 A | | 8/1986 | Gaddy et al. |
| 4,645,658 A | | 2/1987 | Gaddy |
| 4,941,944 A | | 7/1990 | Chang |
| 5,221,357 A | * | 6/1993 | Brink .............................. 127/43 |
| 5,370,999 A | | 12/1994 | Stuart |
| 5,707,673 A | * | 1/1998 | Prevost et al. ................. 426/417 |
| 5,735,916 A | | 4/1998 | Lucas et al. |
| 5,868,851 A | | 2/1999 | Lightner |
| 5,928,616 A | * | 7/1999 | Bailey .......................... 422/256 |
| 6,007,636 A | | 12/1999 | Lightner |
| 6,409,841 B1 | * | 6/2002 | Lombard ........................ 127/37 |
| 6,441,202 B1 | | 8/2002 | Lightner |
| 6,610,831 B1 | * | 8/2003 | McInnis et al. ............... 530/373 |
| 8,382,905 B2 | * | 2/2013 | Takeshima et al. ............. 127/37 |
| 8,603,295 B2 | * | 12/2013 | Dottori et al. .................. 162/22 |
| 8,709,769 B2 | * | 4/2014 | Weydahl ....................... 435/163 |
| 2003/0199049 A1 | | 10/2003 | Nguyen et al. |
| 2009/0229599 A1 | * | 9/2009 | Zhang ............................. 127/1 |
| 2010/0284900 A1 | | 11/2010 | Chen |
| 2011/0294181 A1 | | 12/2011 | Weydahl |
| 2011/0312055 A1 | | 12/2011 | Weydahl |
| 2012/0006320 A1 | * | 1/2012 | Nguyen .......................... 127/34 |
| 2012/0135489 A1 | * | 5/2012 | Weydahl ....................... 435/165 |
| 2013/0017589 A1 | * | 1/2013 | Dottori et al. ................ 435/165 |

FOREIGN PATENT DOCUMENTS

| | | |
|---|---|---|
| GB | 376323 | 7/1932 |
| GB | 602833 A | 6/1948 |
| WO | 9967409 A1 | 12/1999 |
| WO | 0202826 A1 | 1/2002 |
| WO | 2007019505 A2 | 2/2007 |
| WO | 2007051269 A1 | 5/2007 |
| WO | 2007111605 | 10/2007 |
| WO | 2008111045 A1 | 9/2008 |
| WO | 2009036674 A1 | 3/2009 |
| WO | 2010038021 A2 | 4/2010 |
| WO | 2009/036674 A1 | 5/2013 |

OTHER PUBLICATIONS

US Patent & Trademark Office, Notice of Allowance, Examiner-Initiated Interview Summary and Notice of Allowability issued Dec. 20, 2013, and Notice of Allowability and Applicant-Initiated Interview Summary issued Jan. 7, 2014, in co-pending U.S. Appl. No. 13/125,069.
Restriction Requirement issued by the US Patent and Trademark Office in U.S. Appl. No. 13/122,296 on Aug. 9, 2012.
European Patent Office, International Search Report and Written Opinion, Jul. 2, 2010, PCT/GB2009/002333, corresponding to Applicants co-pending U.S. Appl. No. 13/122,296.
European Patent Office, International Search Report and Written Opinion, PCT/GB2009/002349, Nov. 19, 2009, corresponding to Applicants co-pending U.S. Appl. No. 13/125,069.
European Patent Office, International Search Report and Written Opinion, PCT/GB2010/001120, August 17, 2011, corresponding to U.S. Patent Application No. 13/378,655.
United Kingdom Intellectual Property Office, Search Report, British Patent Appln. No. GB 0910707.9, Oct. 9, 2009.
Office Action published in U.S. Appl. No. 13/378,655 on Nov. 16, 2012.
Dempster HS et al. Tracing Organic Contaminants in Groundwater: A New Methodology Using Compound-Specific Isotopic Analysis 1997. Environmental Science and Technology 31:3193-97.
Ege, SN Organic Chemistry: Structure and Reactivity Fifth Edition 2004 p. 159.
Fisher Scientific MSDS for Pentane 2008 pp. 1-7.
Goodwin, "Benzene Thermophysical Properties from 279 to 900 K at Pressures to 1000 Bar" 17:1541-1636 (1988).
Restriction Requirement published in U.S. Appl. No. 13/378,655 on Aug. 23, 2012.
Office Actions published by the US Patent & Trademark Office in co-pending U.S. Appl. No. 13/125,069 on Jan. 17, 2003 and Apr. 18, 2013.
Office Action published by the US Patent & Trademark Office in co-pending U.S. Appl. No. 13/122,296 on Feb. 13, 2013, along with a Notice of References cited issued Feb. 13, 2013.
Gros et al., "High Pressure Phase Equilibrium Modeling of Mixtures Containing Associating Compounds and Gases" Fluid Phase Equilibria 139:75-87 (1997).
Brignole et al., "Supercritical Fluid Extraction of Alcohols from Water" Ind. Eng. Chem. Res. 26:254-261 (1987).
Posthill et al., "Portable Power Sources Using Combustion of Butane and Thermoelectrics" International Conference on Thermoelectrics pp. 520-523 (2005).
United States Patent & Trademark Office: Office Action issued in co-pending U.S. Appl. No. 13/378,655 on Aug. 2, 2013.
European Patent Office (International Search Authority), International Search Report and Written Opinion, PCT/GB2010/000791, Sep. 28, 2010.
United Kingdom Intellectual Property Office, Search Report, United Kingdom Patent Application No. GB0907879.1, Sep. 4, 2009.
U.S. Patent & Trademark Office, Office Action issued on Jul. 31, 2014 in co-pending U.S. Appl. No. 13/378,655.
United States Patent & Trademark Office, "Office Action" and "Interview Summary" issued Nov. 13, 2014 in copending U.S. Appl. No. 13/378,655.
United States Patent & Trademark Office, "Office Action" and "Notice of References Cited" issued Dec. 2, 2014 in copending U.S. Appl. No. 13/122,296.
Bothun thesis, 2004 (cited in the copending '296 application in the above Office Action and Notice of References Cited).
United States Patent & Trademark Office, "Notice of Allowability" and "Interview Summary" issued Mar. 24, 2014 and "Issue Notification" issued Apr. 9, 2014 in US Patent granted in copending U.S. Appl. No. 13/125,069.
United States Patent & Trademark Office, "Office Action" and "Notice of References Cited" issued Jun. 29, 2015 in copending U.S. Appl. No. 13/378,655.

* cited by examiner

PROCESS FOR THE PRODUCTION OF ALCOHOLS

This invention relates to improvements in and relating to processes for the production of alcohols from cellulosic material, in particular rice straw, and to apparatus for use in such processes.

Alcohols, such as ethanol and butanol, produced by fermenting the sugars from waste or biomass, are rapidly becoming a major alternative to hydrocarbons such as natural gas and petroleum. While the current focus is on the production of ethanol from plant seed, e.g. maize, the magnitude of the demand for biofuels threatens a reduction in the land area devoted to food production and a desirable alternative to plant seed as the starting material is plant material other than seed, e.g. grass, wood, paper, maize husks, straw, etc. In this case the alcohol is produced by first breaking down the cellulose and hemicellulose (for convenience both are simply referred to as cellulose herein) into fermentable sugars. This may be done with enzymes but it is achieved most efficiently and economically by hydrolysis with strong acids, for example mineral acids such as sulphuric and hydrochloric acid. However for large scale commercial production of ethanol in this way, a major portion of the acid used must be recovered and recycled.

In WO 02/02826, the contents of which are hereby incorporated by reference, the inventors proposed such an alcohol production process in which the strong acid was recovered by contacting the hydrolysate with an organic extraction solvent, for example methyl ethyl ketone, with separation of the solid lignin and precipitated sugars to yield an acid solution comprising water, extraction solvent, acid and some dissolved sugars. The extraction solvent in the acid solution was then evaporated off under vacuum to be recycled and to leave an aqueous acid and sugar solution which was further evaporated off to yield a concentrated acid/sugar mixture, again for recycling.

For continuous operation, the extraction solvent is fed into the base of a counterflow separation column and the acid-containing extraction solvent is removed from the top of the column while the hydrolysate is fed into the top of the column and a slurry comprising lignin and undissolved oligosaccharides is removed from the base. We have now found that the recovery of the oligosaccharides is enhanced if extraction solvent is introduced into the hydrolysate at at least two points on the oligosaccharide flow path through a separator and if removal of the acid-containing extraction solvent from the separator, e.g. for extraction solvent recovery and reuse, is effected at a point on the flow path between the extraction solvent introduction points.

Thus viewed from one aspect the invention provides a process for alcohol production from a cellulosic material wherein a said cellulosic material is subjected to acid hydrolysis to yield an aqueous hydrolysate, said hydrolysate is introduced into a separator at a hydrolysate inlet, an extraction solvent is introduced into said separator at at least two extraction solvent inlets, a residue containing oligosaccharides is removed from said separator at a residue discharge outlet, and acid-containing extraction solvent is removed from said separator at an extraction solvent discharge outlet, wherein removal of said extraction solvent from said separator through said discharge outlet occurs downstream of at least one said extraction solvent inlet and upstream of at least one other said extraction solvent inlet.

Particularly desirably, the process involves a time delay of at least 10 seconds, more preferably at least 20 seconds, especially at least 30 seconds, more especially at least 60 seconds, e.g. up to 120 seconds, between the earliest point of contact between the hydrolysate and the extraction solvent and that extraction solvent reaching the extraction solvent discharge outlet. Expressed in this way, the invention provides in a further aspect a process for the production of an oligosaccharide-containing residue from a cellulosic material, wherein a said cellulosic material is subjected to acid hydrolysis to yield an aqueous hydrolysate, said hydrolysate is introduced into a separator at a hydrolysate inlet, an extraction solvent is introduced into said separator at an extraction solvent inlet, a residue containing oligosaccharides is removed from said separator at a residue discharge outlet, and acid-containing extraction solvent is removed from said separator at an extraction solvent discharge outlet, wherein said hydrolysate inlet and said extraction solvent discharge outlet are so positioned that the time of flow from said hydrolysate inlet to said extraction solvent discharge outlet is at least 10 seconds.

The time delays for fluids flowing through the separator may readily be calculated for most apparatus or operating conditions. However it may also be determined experimentally by injecting a bolus of a detectable material, e.g. a soluble dye, into the hydrolysate and/or the extraction solvent before it/they enter the separator, and detecting the passage of the marker out of the separator in the discharged extraction solvent. It will be understood that such a marker bolus may not reach the discharge simultaneously and that the mean or, more generally mode, should be used. The time delay will be particularly broadened where baffles or stirrers intervene between the point of entry of the marker and the extraction solvent discharge.

In a particularly preferred embodiment, the extraction solvent is removed at at least two outlets located between the inlets, with the solvent removed at one such outlet being returned to the separator through one of the solvent inlets. Thus, in the oligosaccharide flow direction the solvent inlet and outlet order could be first inlet, first outlet, second outlet then second inlet or, more preferably, second inlet, second outlet, first outlet then first inlet, i.e. where the second outlet is the outlet from which the acid-containing extraction solvent is discharged from the separator, for example for solvent recovery and reuse.

Since an effect of the extraction solvent is to remove acid from the hydrolysate and leave an undissolved residue (which generally contains oligosaccharides and lignin), the residue is generally most readily removed from a base of the separator with the extraction solvent being discharged from at or near the top of the fluid flowing through the separator, the separator will most conveniently take the form of substantially vertical columns connected in series with hydrolysate being fed into the upper part of the first column and the residue being discharged from the base of the final column. In this format, extraction solvent inlets will conveniently be positioned at or near the top of the first column and near the base of the final column and extraction solvent outlets will conveniently be positioned at or near the top of the final column and near the base of the first column. The use of vertical columns however is preferred rather than required—the separator could for example take the form of a tube with alternating upwards and downwards leaning portions, with residue removal being from a final downwards portion and solvent outlets being positioned at the top of upper bends in the tube.

Where the acid-containing extraction solvent is removed from the separator, the separator will preferably be so formed that residue entrainment by the discharged solvent is minimised. Thus for example in one embodiment the discharge outlet may be at the top of a second or subsequent column where the hydrolysate flow into that column occurs lower down the column. Alternatively and preferably the discharge outlet may be in a section of the separator away from the main oligosaccharide flow path. In this case for example the separator may comprise two concentric cylinders with the oligosaccharide flow path being through the top of the inner cylinder, out from the base of the inner cylinder and into the outer cylinder and then out through the base of the outer cylinder. Extraction solvent discharge can then be out from the outer cylinder at a position above the base of the inner cylinder. The cylinders need not of course be coaxial and their precise shape is not critical. This arrangement is particularly suitable for the first column of a multi-column separator.

The separator preferably contains a mixer to ensure thorough mixing of the extraction solvent and the hydrolysate. The mixer may be active, e.g. a stirrer, or passive, e.g. plates, fins or baffles. The use of passive mixers is generally preferred. Where the separator contains more than one column, each is preferably provided with a mixer.

The separator is preferably sealed to prevent fluid exit other than through the residue and solvent outlets.

The separator, if it comprises vertical columns, is preferably provided with baffles or plates to increase residence time in the columns. The area of such plates/baffles preferably increases in the flow direction. Where the separator has baffles or plates on which residue build up could occur, a gap is preferably left between the baffle/plate and the separator wall to reduce the likelihood of this occurring. Likewise it is preferred to arrange an active mixer so as to flush away any residue being deposited on such plates/baffles.

To ensure thorough mixing of extraction solvent and hydrolysate, the separator is preferably provided with one or more pumps to pump solvent or hydrolysate into the separator, or to transfer solvent and/or hydrolysate between columns of a multi-column separator. The separator should of course be built to withstand the pressures, temperature and chemicals used.

Residue discharge may be continuous or, more preferably, batchwise. The separator thus preferably has an isolatable and evacuatable residue collection unit, e.g. as a base portion of the final column of a multi-column separator.

The separator preferably forms part of a larger system in which the acid hydrolysis may also be effected.

Thus viewed from one aspect the invention provides apparatus for oligosaccharide production from a cellulosic material, said apparatus comprising an acid hydrolysis reactor and a separator having an oligosaccharide flow path therethrough, said separator having: a hydrolysate inlet arranged to receive hydrolysate from said reactor; at least two extraction solvent inlets for introduction of an extraction solvent; a residue discharge outlet for removal of a residue containing oligosaccharides; and an extraction solvent discharge outlet for removal of acid-containing extraction solvent, wherein said extraction solvent discharge outlet is downstream on said flow path of at least one said extraction solvent inlet and upstream on said flow path of at least one other said extraction solvent inlet.

The reactor may operate batchwise or, more preferably continuously. For continuous operation, it is conveniently in the form of a conduit with cellulosic material and acid inlet ports at one end and a hydrolysate outlet port at the other. In this format, it is preferably equipped with a screw drive to move the reaction mass from inlet to outlet with a residence time sufficient for the hydrolysis reaction to have been carried out. A conventional reactor may be used.

Besides the separator and the solvent extraction step, the remaining apparatus components and process steps for the conversion of the cellulosic material to alcohol may be conventional; however, exemplary versions will be described herein.

Moreover, it should be noted that the performance of the cellulosic material to alcohol transformation may be divided between two or more sites, for example with oligosaccharide-containing residue production on one site and alcohol production and extraction on another.

Thus viewed from a further aspect the invention provides a process for the production of an oligosaccharide-containing residue from a cellulosic material, wherein a said cellulosic material is subjected to acid hydrolysis to yield an aqueous hydrolysate, said hydrolysate is introduced into a separator at a hydrolysate inlet, an extraction solvent is introduced into said separator at at least two extraction solvent inlets, a residue containing oligosaccharides is removed from said separator at a residue discharge outlet, and acid-containing extraction solvent is removed from said separator at an extraction solvent discharge outlet, wherein removal of said extraction solvent from said separator through said discharge outlet occurs downstream of at least one said extraction solvent inlet and upstream of at least one other said extraction solvent inlet. In a further aspect the invention also provides a process for the production of an oligosaccharide-containing residue from a cellulosic material, wherein a said cellulosic material is subjected to acid hydrolysis to yield an aqueous hydrolysate, said hydrolysate is introduced into a separator at a hydrolysate inlet, an extraction solvent is introduced into said separator at at least two extraction solvent inlets, a residue containing oligosaccharides is removed from said separator at a residue discharge outlet, and acid-containing extraction solvent is removed from said separator at an extraction solvent discharge outlet, wherein said hydrolysate inlet and said extraction solvent discharge outlet are so positioned that the time of flow from said hydrolysate inlet to said extraction solvent discharge outlet is at least 10 seconds.

More particularly, the overall process will generally comprise the following steps:

(i) hydrolyzing the cellulosic material with an aqueous acid to produce a hydrolysate;

(ii) extracting acid and water from the hydrolysate with an extraction solvent to yield (a) a first aqueous acidic solution containing the extraction solvent and (b) a residue containing oligosaccharides;

(iii) subjecting the residue to an oligosaccharide cleavage reaction to yield an aqueous solution of fermentable sugars;

(iv) fermenting the fermentable sugars and distilling alcohol from the resulting fermented mixture;

(v) evaporating the extraction solvent from the first solution to yield (a) a second aqueous acid solution and (b) gaseous extraction solvent;

(vi) optionally, but preferably, condensing the gaseous extraction solvent for recycling; and, optionally but preferably, (vii) concentrating the second aqueous acid solution for recycling.

The extraction step, step (ii), may be effected under ambient or elevated pressure, e.g. 1 to 10 bar, preferably 1 to 6 bar. It will generally be effected at elevated temperature, e.g. 30 to 70° C., preferably 40 to 60° C., especially 50 to 55° C. Preferably, the extraction step is performed at a temperature within 15° C. of that of step (i), especially within 10° C. and a pressure within 1 bar of that of step (i), especially within 0.5 bar.

The evaporation step, step (v), may also be performed at ambient or elevated pressure, e.g. up to 8 bar, preferably 1 to 5 bar, and at a temperature of 25 to 60° C., preferably 40 to 55°

C. The temperature and pressure combination however will be one at which the extraction solvent is gaseous. Preferably, the evaporation step is performed at a temperature within 15° C. of the temperature of step (ii), especially within 10° C. Likewise, the evaporation step is preferably performed at a pressure within 5 bar of that of step (ii), especially within 3 bar. Thus it is preferred to carry out step (ii) under elevated pressure and step (v) under a lower pressure.

The condensation step, step (vi), is preferably effected at a temperature in the range 0 to 60° C., especially 20 to 55° C., and at ambient or elevated pressure, e.g. up to 10 bar, especially up to 6 bar. The temperature and pressure combination however should be one at which the extraction solvent is liquid. Preferably, the condensation step is effected at a temperature within 15° C. of that of step (ii), especially within 10° C., and a pressure within 1 bar of that of step (ii), especially within 0.5 bar. Cooling to effect condensation is preferably effected using water from the local environment, e.g. from a river, a lake or, especially, the sea.

The condensed extraction solvent yielded by step (vi) may of course contain water; however the water content will generally not be so high as to prevent oligosaccharide precipitation in step (ii). If desired, the recycled extraction solvent may be combined with fresh extraction solvent for step (ii).

The extraction solvent may be a single solvent compound or a combination of at least two compounds. The compounds will typically be at least partially water-miscible organic solvents, conveniently solvents selected from alcohols, ethers and ketones with up to eight carbons per molecule; however, other at least partially water-miscible organic solvents may be used. Preferably the compounds are not ones which are highly toxic to yeasts or bacteria as some of the extraction solvent may be carried over to the fermentation step. Examples of preferred compounds include methyl ethyl ketone, acetone, methanol, ethanol, n-propanol, and iso-propanol.

The acid used in the process of the invention may be any strong acid, but will generally be an inorganic acid such as phosphoric or sulphuric acid. The use of sulphuric acid is preferred; the use of hydrochloric acid is generally not preferred. The use of a mixture of sulphuric and phosphoric acids, e.g. in a 1:1 to 4:1 volume ratio, especially about 2:1 volume ratio, is especially preferred.

The acid solution as contacted with the cellulosic starting material preferably corresponds to an acid:water weight ratio of 1:1 to 4:1, especially about 3:1. Acid solutions of the pHs conventionally used in strong acid hydrolysis of cellulosic materials may be used. It should be noted that acid and water may be added separately or that the initial acid added may be diluted or concentrated to yield the desired acid:water balance.

The acid hydrolysis may be performed in conventional fashion. Typically, hydrolysis, which is exothermic, will be performed on a continuous basis, under cooling, e.g. water cooling, to maintain the hydrolysis mixture at 50 to 55° C. The acid solution:cellulosic material ratio is typically 2:1 to 4:1 by weight and the hydrolysis duration will generally be 1 to 4, especially about 2, hours. In this way the cellulose is broken down to produce oligosaccharides which can be precipitated out by the extraction solvent to yield a lignin/sugars slurry.

The slurry residue from the separator may be washed with extraction solvent if desired, it may be drained of liquids if desired, and it may be dried if desired. Alternatively it can be used directly for the oligosaccharide cleavage step after addition of water to bring the sugars into solution. The oligosaccharide cleavage reaction may be effected enzymatically or alternatively, and preferably, by acid hydrolysis. In practice the residue of acid retained in the unwashed slurry is adequate for oligosaccharide cleavage to proceed via such a second acid hydrolysis step. Alternatively further acid may be added, for example to bring the acid content of the sugar solution up to about 0.1 to 5 wt %, especially 0.5 to 2 wt %, particularly about 1 wt %. Addition of excess acid is undesirable as, following a second acid hydrolysis, the resulting hydrolysate must be neutralized to a pH suitable for the microorganisms responsible for fermentation (generally yeasts). This second hydrolysis may be effected under conventional conditions for weak acid hydrolysis of oligosaccharides, e.g. a temperature of about 140° C., a pressure of 5-6 bar and a duration of about two hours.

Before fermentation, the fermentable sugars in aqueous solution are preferably filtered to recover any lignin. This is preferably washed to recover any entrained sugars for fermentation and compressed for use as a fuel, e.g. to provide energy for one or more of the steps in the overall alcohol production process.

The raw cellulosic material may be any convenient cellulosic material, e.g. grass, straw, wood (e.g. sawdust or wood shavings), paper, corn husks, etc. The use of rice straw is especially preferred.

Where the raw cellulosic material is rice straw. the lignin/sugars mixture will contain fine silica particles. These may be recovered by filtration, e.g. using differently sized meshes for lignin and silica or they may be recovered from the residue of the combustion of the lignin. Such silica particles are useful, e.g. as paint additives, pharmaceutical tabletting aids, or catalyst carriers (e.g. for olefin polymerization), and their collection and use form further aspects of the present invention.

The microorganism used in the fermentation step may be any microorganism capable of converting fermentable sugars to alcohol, e.g. brewer's yeast. Preferably however a yeast or yeast mixture is used which can transform the pentoses yielded by holocellulose hydrolysis as well as the hexoses yielded by cellulose hydrolysis. Such yeasts are available commercially. Where fermentation is performed using microorganisms other than brewer's yeast (e.g. *C. beijerinckii* BA101), alcohols other than ethanol, in particular butanol, can be produced and these too can be used as biofuels. The invention covers the production of such other alcohols.

Distillation may be effected in conventional fashion.

The sugars produced using the invention can be fermented or respired by Baker's yeast or other microorganisms yeast to yield many different biological produced compounds such as glycerol, acetone, organic acids (e.g. butyric acid, lactic acid, acetic acid), hydrogen, methane, biopolymers, single cell protein (SCP), antibiotics and other pharmaceuticals. Specific proteins, enzymes or other compounds could also be extracted from cells grown on the sugars. The sugars moreover may be transformed into desired end products by chemical and physical rather than biological means, e.g. reflux boiling of xylose will yield furfural. The invention thus also covers the production of all such other produced compounds besides alcohols.

The apparatus used in the processes of the invention typically comprises: a hydrolysis reactor; a first separator arranged to receive hydrolysate from said reactor and to discharge an oligosaccharides slurry; a second separator arranged to receive an extraction solvent/water mixture from said first separator and to discharge an aqueous acid solution; an acid reservoir arranged to supply acid to said reactor; an extraction solvent reservoir arranged to supply an organic extraction solvent to said first separator; and a condenser arranged to receive said gaseous extraction solvent from said second separator and to discharge said extraction solvent in liquid form for recycling.

The apparatus preferably also comprises components for recycling the acid and extraction solvent, and for feeding cellulosic material to the reactor. Conveniently, it also comprises components for the downstream handling of the oligosaccharides slurry, e.g. further hydrolysis reactors, reservoirs for a base for neutralizing the residual acid, fermentors and distillation units.

To allow for continuous operation of the process when individual steps are performed batchwise, individual units within the apparatus may be duplicated, i.e. with such units being in parallel, so that one may be in operation while the other is being loaded/unloaded. This is particularly the case for the second acid hydrolysis, the fermentation, the distillation, and the lignin separation steps.

Oligosaccharide recovery can also be enhanced by two alternative processes which form further aspects of the present invention. In a first of these aspects, the invention provides a process for alcohol production from a cellulosic material wherein a said cellulosic material is subjected to acid hydrolysis to yield an aqueous hydrolysate, said hydrolysate is introduced into a separator at a hydrolysate inlet, an extraction solvent is introduced into said separator at an extraction solvent inlet, a residue containing oligosaccharides is removed from said separator at a residue discharge outlet, and acid-containing extraction solvent is removed from said separator at an extraction solvent discharge outlet, wherein said hydrolysate inlet and said extraction solvent discharge outlet are positioned above said extraction solvent inlet, said hydrolysate inlet is positioned at or below said extraction solvent discharge outlet, and said separator has an internal cross-sectional area that is higher at said hydrolysate inlet or between said hydrolysate inlet and said extraction solvent discharge outlet than the average between said extraction solvent inlet and said extraction solvent discharge outlet. In the second of these two further aspects, the invention provides a process for alcohol production from a cellulosic material wherein a said cellulosic material is subjected to acid hydrolysis to yield an aqueous hydrolysate, said hydrolysate is introduced into a separator at a hydrolysate inlet, an extraction solvent is introduced into said separator at an extraction solvent inlet, a residue containing oligosaccharides is removed from said separator at a residue discharge outlet, and acid-containing extraction solvent is removed from said separator at an extraction solvent discharge outlet, wherein said hydrolysate inlet is positioned in said separator below at least 10% of the flow path of extraction solvent from said extraction solvent inlet to said extraction solvent discharge outlet. In this context, by a percentage of the flow path is meant a time percentage. This can be calculated theoretically or can be determined experimentally using marker as discussed above.

Alternatively viewed, in a further aspect the invention provides a process for the production of an oligosaccharide-containing residue from a cellulosic material, wherein a said cellulosic material is subjected to acid hydrolysis to yield an aqueous hydrolysate, said hydrolysate is introduced into a separator at a hydrolysate inlet, an extraction solvent is introduced into said separator at an extraction solvent inlet, a residue containing oligosaccharides is removed from said separator at a residue discharge outlet, and acid-containing extraction solvent is removed from said separator at an extraction solvent discharge outlet, wherein said hydrolysate inlet and said extraction solvent discharge outlet are positioned above said extraction solvent inlet, said hydrolysate inlet is positioned at or below said extraction solvent discharge outlet, and said separator has an internal cross-sectional area that is higher at said hydrolysate inlet or between said hydrolysate inlet and said extraction solvent discharge outlet than the average between said extraction solvent inlet and said extraction solvent discharge outlet. Likewise, in another aspect the invention provides a process for the production of an oligosaccharide-containing residue from a cellulosic material, wherein a said cellulosic material is subjected to acid hydrolysis to yield an aqueous hydrolysate, said hydrolysate is introduced into a separator at a hydrolysate inlet, an extraction solvent is introduced into said separator at an extraction solvent inlet, a residue containing oligosaccharides is removed from said separator at a residue discharge outlet, and acid-containing extraction solvent is removed from said separator at an extraction solvent discharge outlet, wherein said hydrolysate inlet is positioned in said separator below at least 10% of the flow path of extraction solvent from said extraction solvent inlet to said extraction solvent discharge outlet.

The apparatus useful for performing these two further aspects of the invention itself forms further aspects of the invention. Thus, viewed from another aspect the invention provides apparatus for oligosaccharide production from a cellulosic material, said apparatus comprising an acid hydrolysis reactor and a separator having an oligosaccharide flow path therethrough, said separator having: a hydrolysate inlet arranged to receive hydrolysate from said reactor; an extraction solvent inlet for introduction of an extraction solvent; a residue discharge outlet for removal of a residue containing oligosaccharides; and an extraction solvent discharge outlet for removal of acid-containing extraction solvent, wherein said hydrolysate inlet and said extraction solvent discharge outlet are positioned above said extraction solvent inlet, said hydrolysate inlet is positioned at or below said extraction solvent discharge outlet, and said separator has an internal cross-sectional area that is higher at said hydrolysate inlet or between said hydrolysate inlet and said extraction solvent discharge outlet than the average between said extraction solvent inlet and said extraction solvent discharge outlet. Viewed from another aspect still the invention provides apparatus for oligosaccharide production from a cellulosic material, said apparatus comprising an acid hydrolysis reactor and a separator having an oligosaccharide flow path therethrough, said separator having: a hydrolysate inlet arranged to receive hydrolysate from said reactor; an extraction solvent inlet for introduction of an extraction solvent; a residue discharge outlet for removal of a residue containing oligosaccharides; and an extraction solvent discharge outlet for removal of acid-containing extraction solvent, wherein hydrolysate inlet is positioned in said separator below at least 10% of the flow path of extraction solvent from said extraction solvent inlet to said extraction solvent discharge outlet.

In the first of these two further aspects, the effect of the non-uniform cross-sectional area separator is to create a region of reduced flow velocity for the extraction solvent at the hydrolysate inlet or between this and the solvent outlet. In this way, saccharide particles are allowed to grow to a level where gravity will prevent them from being entrained with the solvent as it leaves the separator. This non-uniform cross-section may be achieved in numerous ways, e.g. by giving the separator an inverted conical shape or providing it with a side extension into which the hydrolysate inlet opens. However, it is especially preferred to achieve it by having the separator in the form of two joined, coaxial cylinders wthe the upper having a greater diameter. In general, any reduction of the flow rate of the extraction solvent from the vicinity of the hydrolysate inlet to the solvent outlet will increase saccharide recovery—however, the flow rate reduction, relative to the average flow rate from solvent inlet to solvent outlet is preferably 10 to 90%, especially 30 to 80%.

In the second of the two further aspects, the solvent inlet is preferably near the base of the separator (e.g. within 10% of the separator length) and the solvent outlet is preferably at or near the top of the separator, with the hydrolysate inlet preferably being within 50 to 95%, especially 65 to 85%, of the separator length from its base. If desired, the various different aspects of the invention may be combined, e.g. with the hydrolysate inlet part-way up the separator at, near or below a region of reduced solvent flow velocity.

For these two further aspects, the process and apparatus features described earlier in relation to the first aspect may be used wherever compatible.

Where desired, the separator may comprise more than one vessel, and in a particularly preferred embodiment hydrolysate and acidic aqueous extraction solvent are fed into a first separator vessel, acidic aqueous extraction solvent is discharged from that first vessel for extraction solvent recovery, and particle-containing hydrolysate is fed from that first separator vessel into a second separator vessel into which is also fed extraction solvent. From that second vessel, acidic aqueous extraction solvent is fed to the first vessel and lignin-containing solids are discharged. In this format, the first vessel, which is preferably of greater diameter than the second, and which preferably contains a stirrer or other fluid mixing means, effectively functions as a first settling tank. If desired, solids settling out in this first vessel may be removed directly rather than being passed into the second separator vessel.

Embodiments of the invention will now be described further with reference to the following non-limiting Examples and the accompanying drawings, in which.

Figure 1:
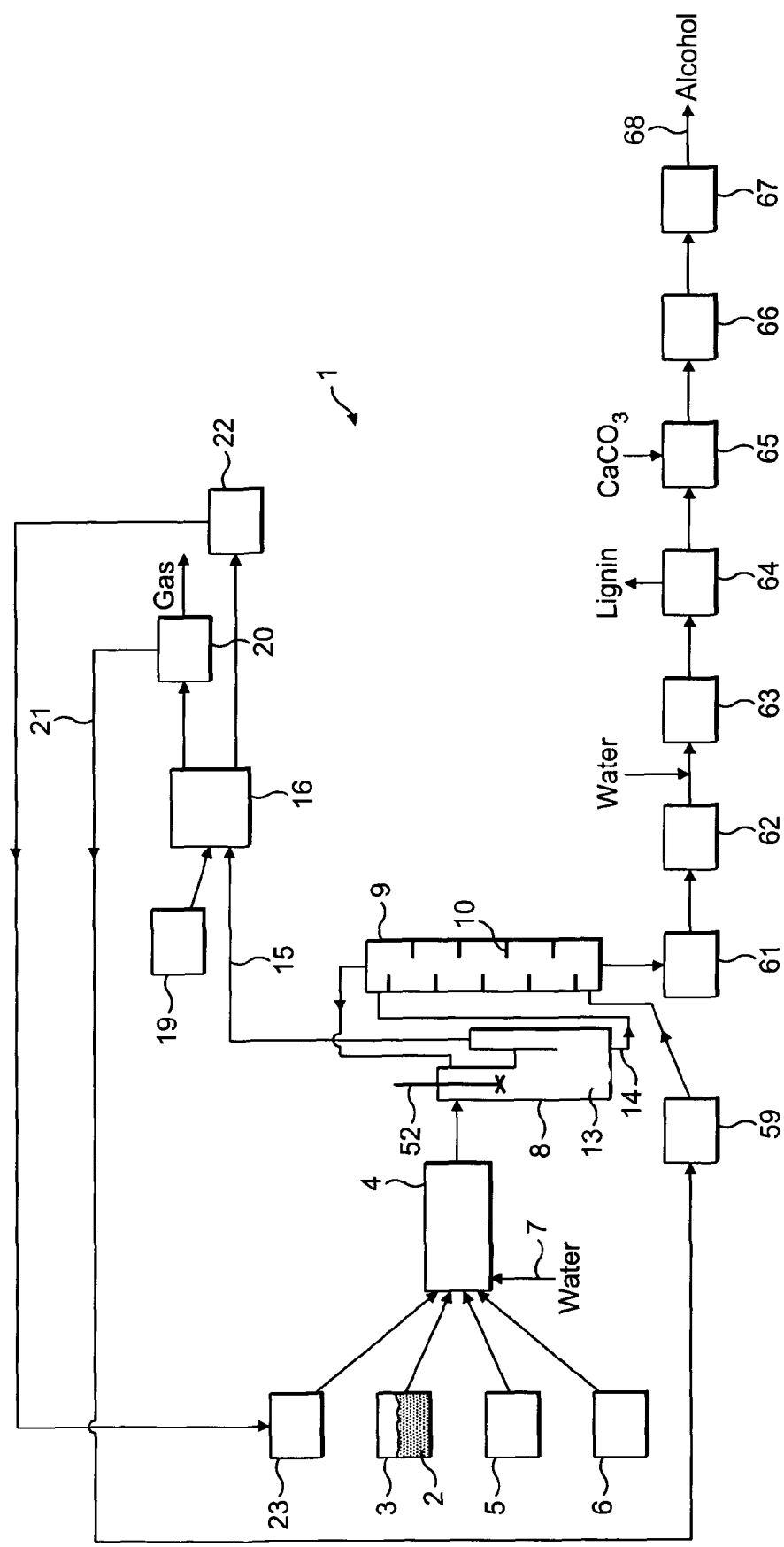
FIG. 1 is a schematic diagram of an apparatus according to the invention.

Referring to FIG. 1, there is shown an apparatus 1 for the conversion of wood pulp to ethanol. Rice straw 2 is fed from hopper 3 into a hydrolysis reactor 4 containing a rotating screw operated to ensure a residence time for the rice straw within the reactor of about two hours. The reactor is provided with a water-cooling jacket to maintain the hydrolysis mixture at about 50-55° C. Sulphuric and phosphoric acids and water, in a weight ratio of 2:1:1 are fed into reactor 4 from reservoirs 5 and 6, water feed line 7, and acid recycling reservoir 23. The hydrolysate from reactor 4 is fed to the top of a first separation column 8 and from outlet 14 in the base of the first column 8 to the top of a second, counterflow separation column 9 which has internal plates 10 to delay through flow. Into the base of column 9 is introduced an organic extraction solvent, e.g. methyl ethyl ketone, from reservoir 59. Within the column 9, water and acid are taken up by the extraction solvent and lignin and precipitated oligosaccharides are passed from the base of the column to a continuous filtration unit 61. The acid/water/extraction solvent mixture is discharged from the top of column 9 and fed into the top of the first separator column 8 which is equipped with a mixer 52. The base of column 8 has a chamber 13 with outlet 14 at its base and a further discharge outlet 15 at its top from which the extraction solvent is removed to be passed into a third separator column 16.

The solid residue from filtration unit 61 is passed to a drier 62 and the dry lignin/oligosaccharides mixture is then dissolved in water and passed into a second hydrolysis reactor 63. The liquid from the filtration unit 61 is passed to separator column 16.

In the second reactor 63, a further acid hydrolysis is effected at 140° C. for two hours at 5-6 bar. The hydrolysate is filtered in filtration unit 64 to remove lignin (which is compressed and combusted to provide energy for the overall apparatus). The remaining solution of fermentable sugars is neutralized with calcium carbonate in neutralization unit 65 before being passed to fermentation unit 66 where brewers' yeast is added and fermentation is allowed to take place. The fermented mixture is then fed to distillation unit 67 where ethanol is distilled off via line 68.

The acid/water/extraction solvent in separator column 16 is depressurized to cause the extraction solvent to evaporate. The gaseous extraction solvent is led from separator column 16 to a condenser 20 where the pressure is increased sufficiently to liquefy the extraction solvent and the liquid extraction solvent is recycled via line 21 to reservoir 59. The remaining aqueous acid is fed from separator column 16 to evaporator unit 22 where water is removed under vacuum. The remaining acid, containing some dissolved sugar, is recycled to reservoir 23.

Figure 2:
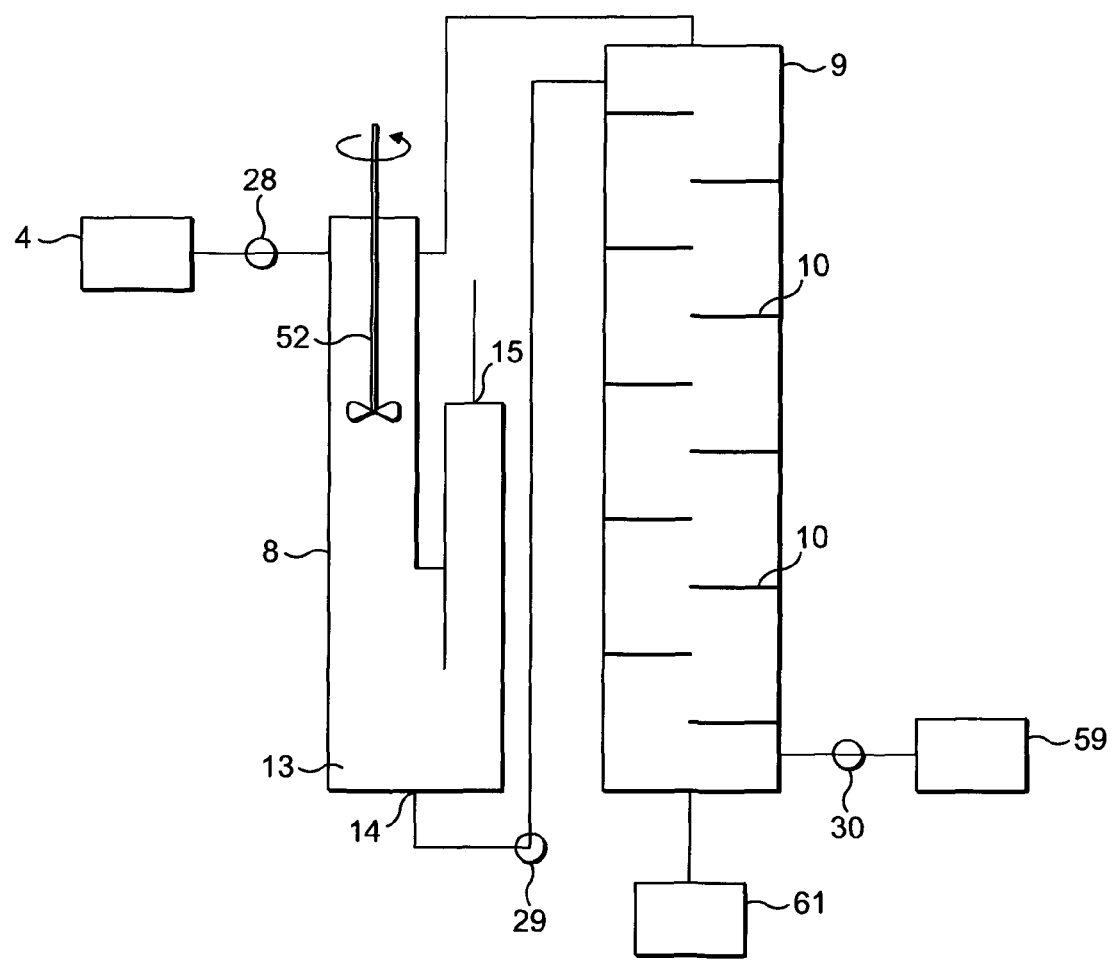
FIG. 2 is a schematic diagram of a twin column separator useful for a first process of the invention.

Referring to FIG. 2 there is shown in more detail the separator shown in FIG. 1 including pumps 28 and 29 used to transfer hydrolysate and pump 30 used to inject extraction solvent.

Figure 3:
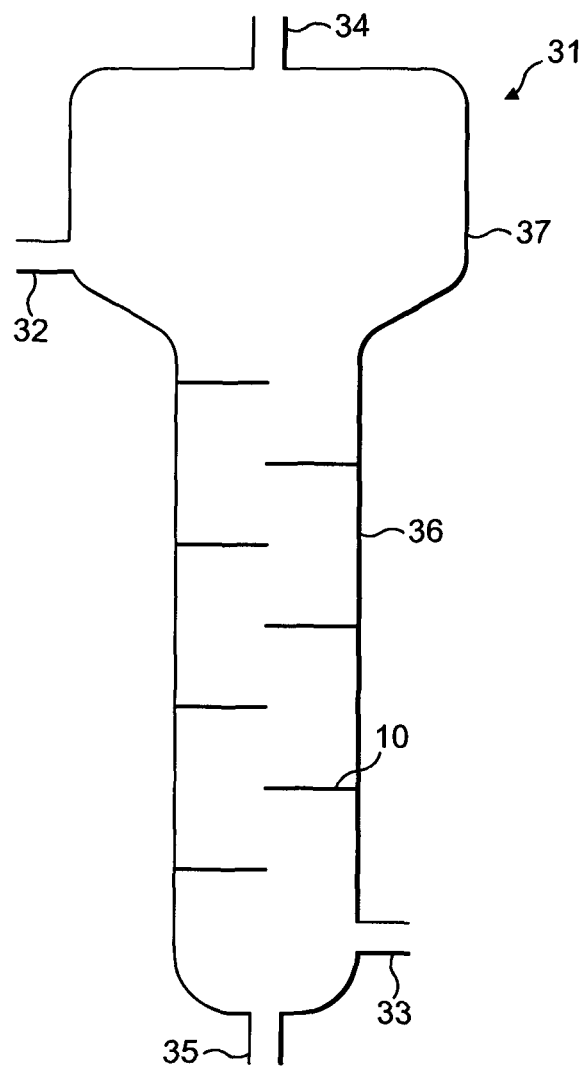
FIG. 3 is a schematic diagram of a non-uniform diameter separator useful for a further process of the invention.

Referring to FIG. 3, there is shown a separator 31 having hydrolysate inlet 32, extraction solvent inlet 33, extraction solvent discharge outlet 34, and residue discharge outlet 35. The separator is in the form of two joined vertical cylinders 36 and 37, the upper of which has a greater diameter so as to reduce solvent flow velocity before the solvent outlet is reached. Within the separator are disposed plates 10 as in FIG. 1.

Figure 4:
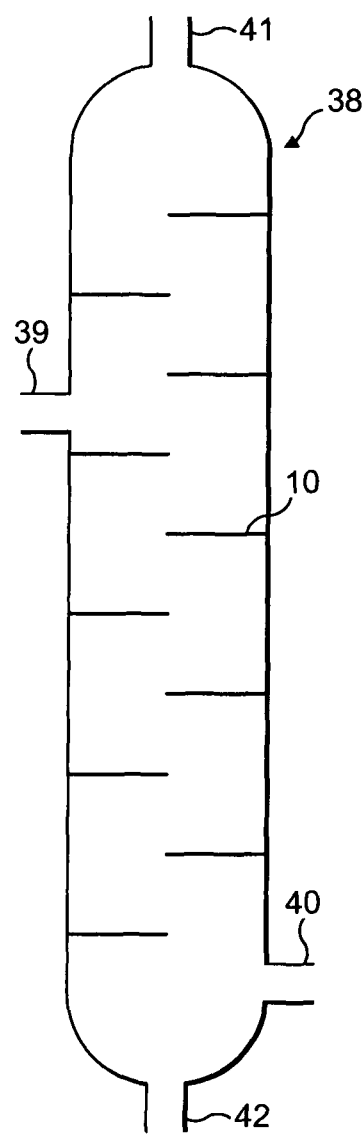
FIG. 4 is a schematic diagram of a further separator useful for a process of the invention.

Referring to FIG. 4, there is shown a separator 38 having hydrolysate inlet 39, extraction solvent inlet 40, extraction solvent discharge outlet 41, and residue discharge outlet 42. The separator is generally cylindrical with the hydrolysate inlet positioned sufficiently much lower than the solvent outlet as to permit saccharide particle growth to occur and saccharide precipitation to occur in the zone between hydrolysate entry and solvent exit. Within the separator are disposed plates 10 as in FIG. 1.

Figure 5:
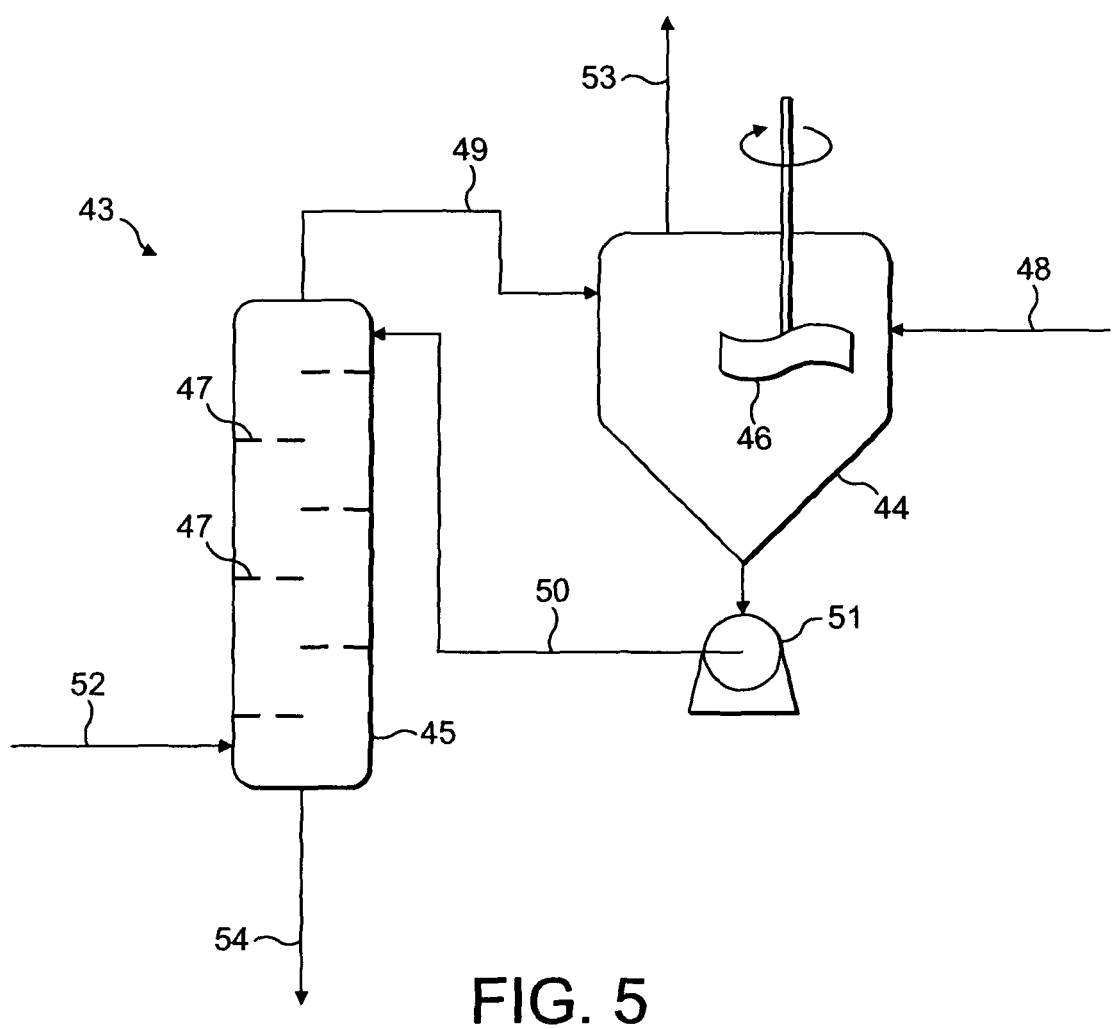
FIG. 5 is a schematic diagram of a further non-uniform diameter separator useful for a further process of the invention.

Referring to FIG. 5, there is shown a separator 43 comprising a settling tank 44 and a separator column 45, the former equipped with a stirrer 46 and the latter with plates 47. Settling tank 44 receives hydrolysate through hydrolysate inlet 48 and aqueous acidic extraction solvent from the separator column via conduit 49. The hydrolysate and extraction solvent are mixed by stirrer 46 causing some precipitation of solids. The solids and the hydrolysate are transferred from settling tank 44 via conduit 50 using a pump 51. Fresh (or recycled) extraction solvent is fed into the base of column 45 through inlet 52 and acidic aqueous extraction solvent is discharged from the top of column 45 via conduit 49 into settling tank 44 from which the acidic aqueous extraction solvent is discharged via outlet 53 for extraction solvent recovery. Solids, i.e. sugars and lignin, are discharged from the base of column 45 via outlet 54.

The invention claimed is:

1. A process for alcohol production from a cellulosic material or for the production of an oligosaccharide-containing residue from a cellulosic material comprising the steps of subjecting a said cellulosic material to acid hydrolysis to yield an aqueous hydrolysate, introducing said hydrolysate into a separator at a hydrolysate inlet, said separator having at least two sections; introducing an extraction solvent into at least two separator sections at at least two extraction solvent inlets, removing a residue containing oligosaccharides from said separator at a residue discharge outlet, and removing acid-containing extraction solvent from said separator at an extraction solvent discharge outlet, wherein removal of said extraction solvent from said separator through said discharge outlet occurs downstream of at least one said extraction solvent inlet and upstream of at least one other said extraction solvent inlet.

2. The process of claim 1, wherein when said extraction solvent is removed at at least 2 outlets located between the extraction solvent inlets, extraction solvent removed at one such outlet is returned to the separator through one of the inlets.

3. The process of claim 2, wherein in oligosaccharide flow direction the solvent inlet and outlet order is second inlet, second outlet, first outlet, first inlet; and wherein the second outlet is the outlet from which the acid-containing extraction solvent is discharged from the separator.

4. The process of claim 1, further comprising a time delay of at least 10 seconds between the earliest point of contact between the hydrolysate and the extraction solvent and said acid containing extraction solvent reaching the extraction solvent discharge outlet.

5. The process of claim 4, wherein said time delay is at least 60 seconds.

6. The process of claim 1, wherein said extraction solvent comprises a ketone having up to eight carbons per molecule.

7. The process of claim 6, wherein said extraction solvent comprises methyl ethyl ketone.

8. The process of claim 1, wherein said acid hydrolysis is with an inorganic acid, and wherein said extraction solvent comprises an ether and/or a ketone having up to 8 carbons per molecule.

9. A process for alcohol production from a cellulosic material or for the production of an oligosaccharide-containing residue from a cellulosic material, comprising the steps of subjecting a said cellulosic material to acid hydrolysis to yield an aqueous hydrolysate, introducing said hydrolysate into a separator at a hydrolysate inlet, said separator having at least two sections; introducing an extraction solvent into at least two separator sections at an extraction solvent inlet, removing a residue containing oligosaccharides from said separator at a residue discharge outlet, and removing acid-containing extraction solvent from said separator at an extraction solvent discharge outlet, wherein:

(a) said hydrolysate inlet and said extraction solvent discharge outlet are so positioned that the time of flow from said hydrolysate inlet to said extraction solvent discharge outlet is at least 10 seconds; or (b) said hydrolysate inlet and said extraction solvent discharge outlet are positioned above said extraction solvent inlet, said hydrolysate inlet is positioned at or below said extraction solvent discharge outlet, and said separator has an internal cross-sectional area that is higher at said hydrolysate inlet or between said hydrolysate inlet and said extraction solvent discharge outlet than the average between said extraction solvent inlet and said extraction solvent discharge outlet; or (c) said hydrolysate inlet is positioned in said separator below at least 10% of the flow path of extraction solvent from said extraction solvent inlet to said extraction solvent discharge outlet.

10. The process of claim 9, wherein said extraction solvent comprises a ketone having up to eight carbons per molecule.

11. The process of claim 10, wherein said extraction solvent comprises methyl ethyl ketone.

12. The process of claim 9, further comprising a time delay of at least 60 seconds between the earliest point of contact between the hydrolysate and the extraction solvent and said acid containing extraction solvent reaching the extraction solvent discharge outlet.

13. Apparatus for oligosaccharide production from a cellulosic material, said apparatus comprising an acid hydrolysis reactor and a separator having an oligosaccharide flow path therethrough, said separator having: a hydrolysate inlet arranged to receive hydrolysate from said reactor; at least two sections with at least two of the sections having an extraction solvent inlet for introduction of an extraction solvent; a residue discharge outlet for removal of a residue containing oligosaccharides; and an extraction solvent discharge outlet for removal of acid-containing extraction solvent, wherein said extraction solvent discharge outlet is downstream on said flow path of at least one said extraction solvent inlet and upstream on said flow path of at least one other said extraction solvent inlet; and wherein said hydrolysate inlet and said extraction solvent discharge outlet are positioned above said extraction solvent inlets, said hydrolysate inlet is positioned at or below said extraction solvent discharge outlet, and said separator has an internal cross-sectional area that is higher at said hydrolysate inlet or between said hydrolysate inlet and said extraction solvent discharge outlet than the average between said extraction solvent inlets and said extraction solvent discharge outlet.

14. The apparatus according to claim 13 for alcohol production from a cellulosic material.

15. The apparatus of claim 13, said apparatus comprising at least two outlets located between the extraction solvent inlets, with the solvent removal at one such outlet being returned to the separator through one of the inlets.

16. The apparatus of claim 15, wherein in the oligosaccharide flow direction the solvent inlet and outlet order is second inlet, second outlet, first outlet, first inlet; and wherein the second outlet is the outlet from which the acid-containing extraction solvent is discharged from the separator.

17. The apparatus of claim 13, wherein said apparatus involves a time delay of at least 10 seconds between the earliest point of contact between the hydrolysate and the extraction solvent and said acid containing extraction solvent reaching the extraction solvent discharge outlet.

18. The apparatus of claim 17, wherein said time delay is at least 60 seconds.

19. The apparatus of claim 13, wherein said extraction solvent comprises a ketone having up to eight carbons per molecule.

20. The apparatus of claim 19, wherein said extraction solvent comprises methyl ethyl ketone.

21. The apparatus of claim 13, wherein said acid hydrolysis reactor is for use with inorganic acid, and said extraction solvent comprises an ether and/or ketone having up to 8 carbons per molecule.

22. Apparatus for oligosaccharide production from a cellulosic material, said apparatus comprising an acid hydrolysis reactor and a separator having an oligosaccharide flow path therethrough, said separator having: a hydrolysate inlet arranged to receive hydrolysate from said reactor; at least two sections, with an extraction solvent inlet for introduction of an extraction solvent; a residue discharge outlet for removal of a residue containing oligosaccharides; and an extraction solvent discharge outlet for removal of acid-containing extraction solvent, wherein said hydrolysate inlet and said extraction solvent discharge outlet are positioned above said extraction solvent inlet, said hydrolysate inlet is positioned at or below said extraction solvent discharge outlet, and said separator has an internal cross-sectional area that is higher at said hydrolysate inlet or between said hydrolysate inlet and said extraction solvent discharge outlet than the average between said extraction solvent inlet and said extraction solvent discharge outlet.

23. The apparatus according to claim 22 for alcohol production from a cellulosic material.

24. The apparatus of claim 22, wherein said extraction solvent comprises a ketone having up to eight carbons per molecule.

25. The apparatus of claim 24, wherein said extraction solvent comprises methyl ethyl ketone.

26. The apparatus of claim 22, wherein said apparatus involves a time delay of at least 60 seconds between the earliest point of contact between the hydrolysate and the extraction solvent and said acid containing extraction solvent reaching the extraction solvent discharge outlet.

27. The apparatus of claim 22, wherein said hydrolysate inlet is positioned in said separator below at least 10% of the flow path of extraction solvent from said extraction solvent inlet to said extraction solvent outlet.

\* \* \* \* \*